US008222042B2

(12) United States Patent
Dugan et al.

(10) Patent No.: US 8,222,042 B2
(45) Date of Patent: Jul. 17, 2012

(54) INTERACTIVE SECURITY SCREENING SYSTEM

(75) Inventors: Regina Elvira Dugan, Rockville, MD (US); Khaled F Eltomi, Rockville, MD (US); Thomas Emory McVeigh, Shenandoah Junction, WV (US); Jack Kotowicz, Washington, DC (US)

(73) Assignee: RedXdefense, LLC, Rockville, MD (US)

( * ) Notice: Subject to any disclaimer, the term of this patent is extended or adjusted under 35 U.S.C. 154(b) by 0 days.

(21) Appl. No.: 12/956,428

(22) Filed: Nov. 30, 2010

(65) Prior Publication Data

US 2011/0095898 A1    Apr. 28, 2011

Related U.S. Application Data

(62) Division of application No. 11/525,344, filed on Sep. 22, 2006, now Pat. No. 7,862,776.

(60) Provisional application No. 60/756,573, filed on Jan. 6, 2006.

(51) Int. Cl.
*G01N 7/00* (2006.01)
*G08B 21/00* (2006.01)

(52) U.S. Cl. .................. 436/148; 422/82.13; 340/540

(58) Field of Classification Search .............. 436/148; 422/82.13; 340/540
See application file for complete search history.

(56) References Cited

U.S. PATENT DOCUMENTS

| 4,219,092 | A |  | 8/1980 | Richter |  |
|---|---|---|---|---|---|
| 4,577,345 | A |  | 3/1986 | Abramov |  |
| 4,788,039 | A |  | 11/1988 | Glattstein |  |
| 5,138,889 | A |  | 8/1992 | Conrad |  |
| 5,157,261 | A |  | 10/1992 | Grey et al. |  |
| 5,296,380 | A |  | 3/1994 | Margalit |  |
| 5,476,794 | A |  | 12/1995 | O'Brien et al. |  |
| 5,480,612 | A |  | 1/1996 | Margalit |  |
| 5,483,601 | A |  | 1/1996 | Faulkner |  |
| 5,566,327 | A |  | 10/1996 | Sehr |  |
| 5,571,976 | A |  | 11/1996 | Drolet |  |
| 5,648,047 | A |  | 7/1997 | Kardish et al. |  |
| 5,741,984 | A |  | 4/1998 | Danylewych-May et al. |  |
| 5,818,047 | A |  | 10/1998 | Chaney et al. |  |
| 5,828,773 | A | * | 10/1998 | Setlak et al. | 382/126 |
| 5,859,375 | A |  | 1/1999 | Danylewych-May et al. |  |
| 5,866,430 | A |  | 2/1999 | Grow |  |
| 6,061,464 | A | * | 5/2000 | Leger | 382/124 |
| 6,073,499 | A |  | 6/2000 | Settles |  |
| 6,078,928 | A |  | 6/2000 | Schnase et al. |  |

(Continued)

FOREIGN PATENT DOCUMENTS

JP     9-126965    5/1997

(Continued)

*Primary Examiner* — Lore Jarrett
(74) *Attorney, Agent, or Firm* — Diederiks & Whitelaw, PLC

(57) ABSTRACT

An interactive security screening system includes a main housing, a contact or palm pad provided on the main housing and a sample sheet positioned upon the contact pad. A sensor is operatively connected to the contact pad to measure pressure applied to the contact pad during a sample collection process. A feedback system, operatively connected to the contact pad and the sensor, provides the subject or screener with at least one of a visual signal and an audio signal to indicate whether requisite pressure was applied to the contact pad. A sample processing system analyzes the sample collection sheet through series, parallel or image processing to determine whether the trace residue sample contains a threat residue. The screening system also employs a spatial recognition system that focuses the sample processing system on particular portions of the sample collection sheet to increase overall system accuracy.

20 Claims, 6 Drawing Sheets

U.S. PATENT DOCUMENTS

| | | |
|---|---|---|
| 6,424,264 B1 | 7/2002 | Giraldin et al. |
| 6,446,514 B1 | 9/2002 | Danylewych-May et al. |
| 6,449,035 B1 | 9/2002 | Batchelder |
| 6,529,786 B1 | 3/2003 | Sim |
| 6,610,977 B2 | 8/2003 | Megerle |
| 6,613,576 B1 | 9/2003 | Rodacy et al. |
| 6,914,668 B2 | 7/2005 | Brestel et al. |
| 6,937,147 B2 | 8/2005 | Dilbeck et al. |
| 6,952,163 B2 | 10/2005 | Huey et al. |
| 6,976,032 B1 | 12/2005 | Hull et al. |
| 7,047,829 B2 | 5/2006 | Napoli |
| 7,116,798 B1 | 10/2006 | Chawla |
| 7,136,513 B2 | 11/2006 | Waehner et al. |
| 7,545,280 B2 | 6/2009 | Dugan et al. |
| 2002/0070863 A1 | 6/2002 | Brooking |
| 2002/0070865 A1 | 6/2002 | Lancos et al. |
| 2002/0082897 A1 | 6/2002 | Menelly et al. |
| 2003/0128100 A1 | 7/2003 | Burkhardt et al. |
| 2003/0130035 A1 | 7/2003 | Kanarat |
| 2003/0142853 A1 | 7/2003 | Waehner et al. |
| 2003/0197853 A1 | 10/2003 | Fenrich |
| 2004/0169589 A1 | 9/2004 | Lea et al. |
| 2004/0230437 A1 | 11/2004 | Havrilak, Jr. |
| 2004/0252024 A1 | 12/2004 | Huey et al. |
| 2004/0265169 A1 | 12/2004 | Haas et al. |
| 2005/0019220 A1 | 1/2005 | Napoli |
| 2005/0024204 A1 | 2/2005 | Germaine et al. |
| 2005/0043897 A1 | 2/2005 | Meyer |
| 2005/0045710 A1 | 3/2005 | Burke et al. |
| 2005/0057354 A1 | 3/2005 | Jenkins et al. |
| 2005/0074147 A1 | 4/2005 | Smith et al. |
| 2005/0081655 A1 | 4/2005 | Fine et al. |
| 2005/0101027 A1 | 5/2005 | Haas |
| 2005/0137890 A1 | 6/2005 | Bhatt et al. |
| 2005/0190058 A1 | 9/2005 | Call |
| 2005/0251398 A1 | 11/2005 | Zanovitch et al. |
| 2005/0256724 A1 | 11/2005 | Rasin et al. |
| 2005/0264416 A1 | 12/2005 | Maurer |
| 2005/0270158 A1 | 12/2005 | Corbett, Jr. |
| 2005/0287036 A1 | 12/2005 | Eckels et al. |
| 2005/0288937 A1 | 12/2005 | Verdiramo |
| 2006/0000903 A1 | 1/2006 | Barry et al. |
| 2006/0015503 A1 | 1/2006 | Simons et al. |
| 2006/0017541 A1 | 1/2006 | Nguyen |
| 2006/0042407 A1* | 3/2006 | Napoli ............... 73/863.12 |

FOREIGN PATENT DOCUMENTS

| | | |
|---|---|---|
| WO | WO 03/034058 | 4/2003 |
| WO | WO 2004/104559 | 12/2004 |
| WO | WO 2006/026107 | 3/2006 |

* cited by examiner

INTERACTIVE SECURITY SCREENING SYSTEM

CROSS-REFERENCE TO RELATED APPLICATION

The present application represents a divisional application of U.S. patent application Ser. No. 11/525,344, filed Sep. 22, 2006 which claims the benefit of U.S. Provisional Patent Application Ser. No. 60/756,573 filed Jan. 6, 2006 entitled "System and Method for Optimization of Trace Chemical Sample Collection and Analysis in Personnel Screening and Security Systems."

BACKGROUND OF THE INVENTION

1. Field of the Invention

The present invention pertains to the art of security screening systems and, more particularly, to an interactive security screening system that focuses a sample processing system on particular portions of a collected sample and employs one or more processes to screen the collected sample for threat residue.

2. Discussion of the Prior Art

Since Sep. 11, 2001, protection against terrorist threats has become a national priority. This priority extends from the protection of government facilities inside the U.S. and abroad to the protection of private businesses and venues. Various types of threats have been postulated, including attacks using explosive, chemical and biological agents, as well as nuclear and radiological (dirty) bombs. The diversity of this threat has created complex security challenges for national, state, and local governments, the transportation industry, private businesses, and even individuals. Total expenditures related to Homeland Security topped $100B in one year and billions more have been allocated in Federal, Supplemental Appropriations, and State/Local spending. Increasingly, U.S. businesses are devoting more revenue to security systems, with expenditures reaching tens of billions. Growth in the homeland security industry is expected to be vigorous over the next decade. Motivated by the wide diversity of potential threats and by the inadequacy of currently available systems, government investments in research and development are strong.

Of the various threats postulated, explosives remain the number one choice of terrorists. Indeed, many experts and reports have noted that, in the case of terrorist activity, the statistical evidence is compelling, the primary threat is bombs. At present, two types of detection systems are in use to combat this threat, i.e., bulk detection systems and trace detection systems. Bulk detection systems identify the presence of a large or threat quantity of explosives. In contrast, trace detection systems identify the presence of residual contamination associated with explosives. That is, trace detection identifies whether an object or person has come into contact with or handled explosives.

Bulk systems can cost more than $1M per portal, while trace detection system generally run in the order of tens of thousands of dollars. Often times, installation and annual maintenance costs will exceed the original price of the system. In the case of trace explosive detection, currently deployed systems were developed primarily for the use of analytical chemists in laboratories and only later adapted for field use. Unfortunately, these systems suffer from long clearance times following a positive detection (15-30 minutes), have exceedingly high false alarm rates and require extensive training to ensure proper use and maintenance. Given the high price associated with the use of bulk detection systems and their lack of suitability for many screening tasks, such as the screening of people, trace detection systems are used with increased frequency and are most often selected for applications outside of aviation security.

The use of trace explosive detection systems is based on widely accepted scientific evidence indicating that handling or otherwise contacting explosives leaves trace residue on hands, clothes, and other materials or surfaces. The trace residue is of a high concentration and is difficult to eradicate. The entire justification for the Federal Aviation Administration's trace explosive detection program is based on this fact. Indeed, contamination is expected to be so extensive and difficult to eliminate that currently installed aviation trace explosive detection systems depend on secondary contamination, i.e., contamination transferred from an individual's hands and clothes to their baggage. Thus, the baggage is sampled for trace explosives and subjected to detection systems for analysis. While currently deployed trace detection systems have high sensitivity, the systems suffer from high operational burdens, poor sampling efficiencies, high false alarm rates and low throughput.

It is known that explosive contamination can vary widely over small spatial distances. Studies have shown that trace residue levels can differ by 10,000 fold over distances as small as a few centimeters. Unfortunately, currently available trace explosive detection systems sample only from limited spatial areas, retain no sample spatial information and recover samples from only a small section of the sample acquisition surface. By sampling from only a small area, often times trace residue is not detected even when present at detectable levels elsewhere on the sample acquisition surface. In addition, currently available sample acquisition methods are not optimized to collect particulates in the size and size range distribution most pertinent for explosives detection. In particular, most conventional trace detection systems, such as ion mobility spectrometers, require that the sample acquisition surface be clear of substances that could interfere with the measurement. Unfortunately, many substances that would improve the efficiency of sample recovery, such as adhesives, are not compatible with conventional systems and therefore cannot be utilized.

The need for a pristine sample acquisition surface or medium has resulted in two primary sample acquisition methods employed in existing trace detection systems such as swabbing (or swiping) an object and air jets that dislodge and test residue from an object. However, both of these methods are limited in sample recovery efficiency and, as stated above, fail to retain any of the spatial information of the sample or surface. Simple swabbing (or swiping) methods tend to leave large particles on the surface, typically recovering only smaller particles. Other methods, such as the above described air jet systems, often times dislodge larger particles, but leave smaller particles on the surface. Simply put, both of these techniques fail to recover a significant fraction of the existing trace contamination.

In addition to the above described shortcomings, problems exist with sample reproducibility when using swabbing techniques. Extensive operator training is required to achieve even moderately reproducible results. The required operator training not only significantly increases operational costs, but the intensity of operator involvement required to obtain a good and consistent sample significantly reduces throughput rates. In any case, additional information, particularly more detailed information regarding a likely spatial distribution of trace sample collection, would not only improve the probability of detection but, by eliminating areas that are not relevant and by permitting image analysis as a secondary level of processing, also improve the signal-to-noise ratio. Currently available systems do not permit such resolution.

Finally, existing systems do not to provide feedback to the operator or subject as to the reliability of contact or the force applied during contact (which can impact collection efficiency) and, as such, often fail to achieve adequate sample recovery. In addition to preserving some spatial information about the sample, there is also a need to determine where, on the sampling surface, the trace contamination is most likely to be present. In conventional swabbing systems and in novel systems that enable wider area analysis, such information would improve the signal-to-noise ratio of the analysis by focusing the detection and analysis on the area with the highest likelihood of contamination and by eliminating background signals that can cause unnecessary false alarms.

Therefore, despite the existence in the art of security screening systems, there still exists a need for an improved security screening system. More specifically, there exists a need for an interactive security screening system that provides feedback to test subjects and focuses detection on portions of a sample that are most likely to contain trace or threat residue.

SUMMARY OF THE INVENTION

The present invention is directed to a interactive security screening system including a main housing, a contact pad provided in the main housing and a sample collection sheet positioned upon the contact pad. To initiate a screening process, a subject is asked to contact the sample collection sheet which then collects and retains a trace residue sample for analysis. A sensor is operatively connected to the contact pad and configured to measure a pressure applied to the contact pad during a sample collection process. In accordance with the invention, the screening system includes a feedback system operatively connected to the contact pad and the sensor. The feedback system provides the subject or screener with at least one of a visual signal and an audio signal indicating whether a proper sample has been collected.

Once a proper sample is collected, the sample is passed to a sample processing system which scans and analyzes the sample collection sheet to determine whether the trace residue sample contains a threat residue. The sample processing system includes an analyzing portion that employs series processing when maximum scanning accuracy is desired, parallel processing when maximum throughput is necessary or image processing when it is particularly advantageous to remove areas which are not of interest from the sample prior to screening or evaluation. Regardless, the screening system employs a spatial recognition system that focuses the analyzing portion on particular sections of the sample. In this manner, the overall accuracy of the screening system is increased, thereby resulting in fewer false positive results which tend to slow the scanning process, inconvenience individuals and place an unnecessary burden on security personnel.

Additional objects, features and advantages of the present invention will become more readily apparent from the following detailed description of preferred embodiments when taken in conjunction with the drawings wherein like reference numerals refer to corresponding parts in the several views.

DETAILED DESCRIPTION OF THE PREFERRED EMBODIMENTS

Figure 1:
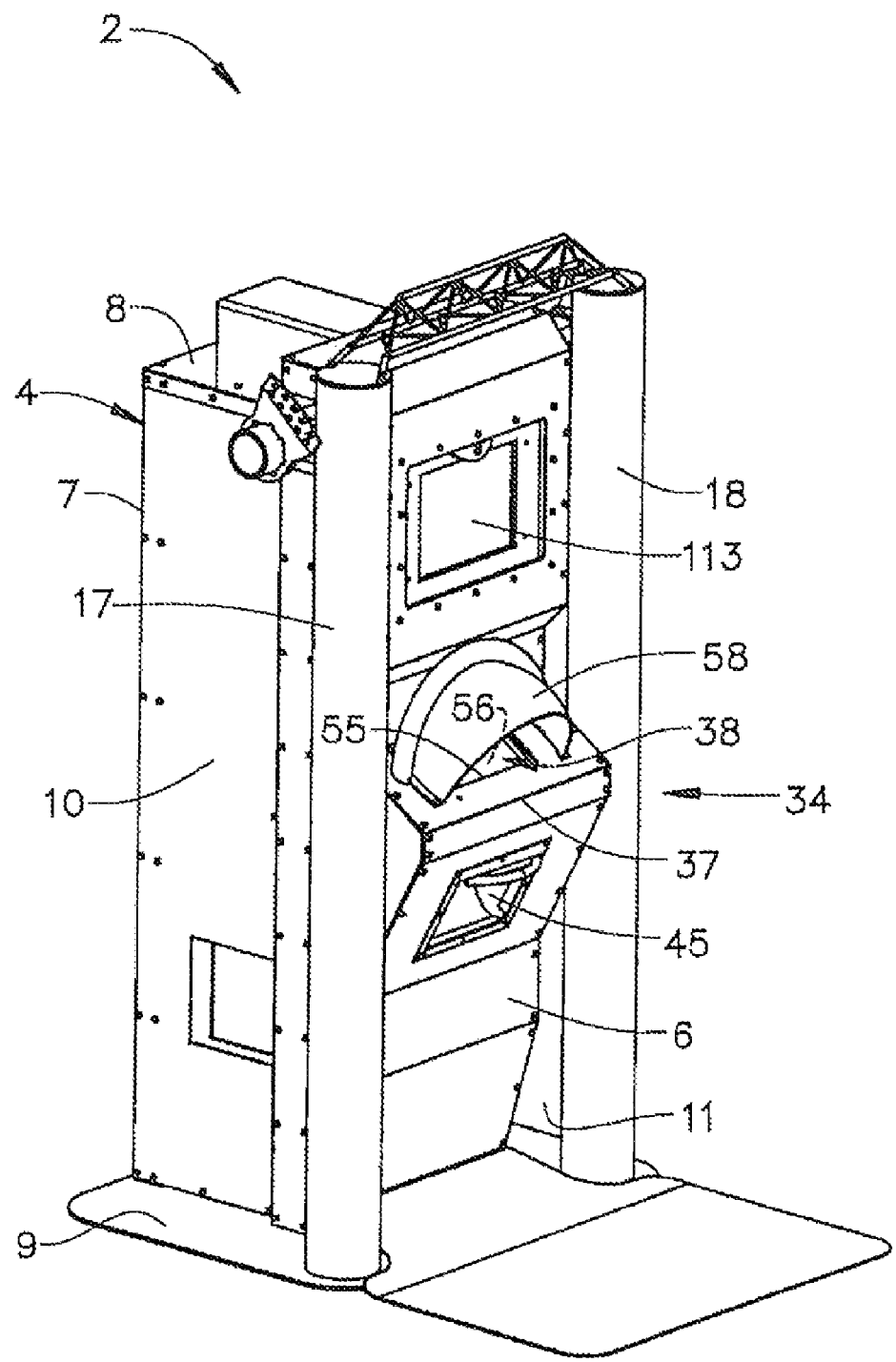
FIG. 1 is an upper left perspective view of a screening center including a dynamic user feedback and processing system constructed in accordance with the present invention.
Figure 2:
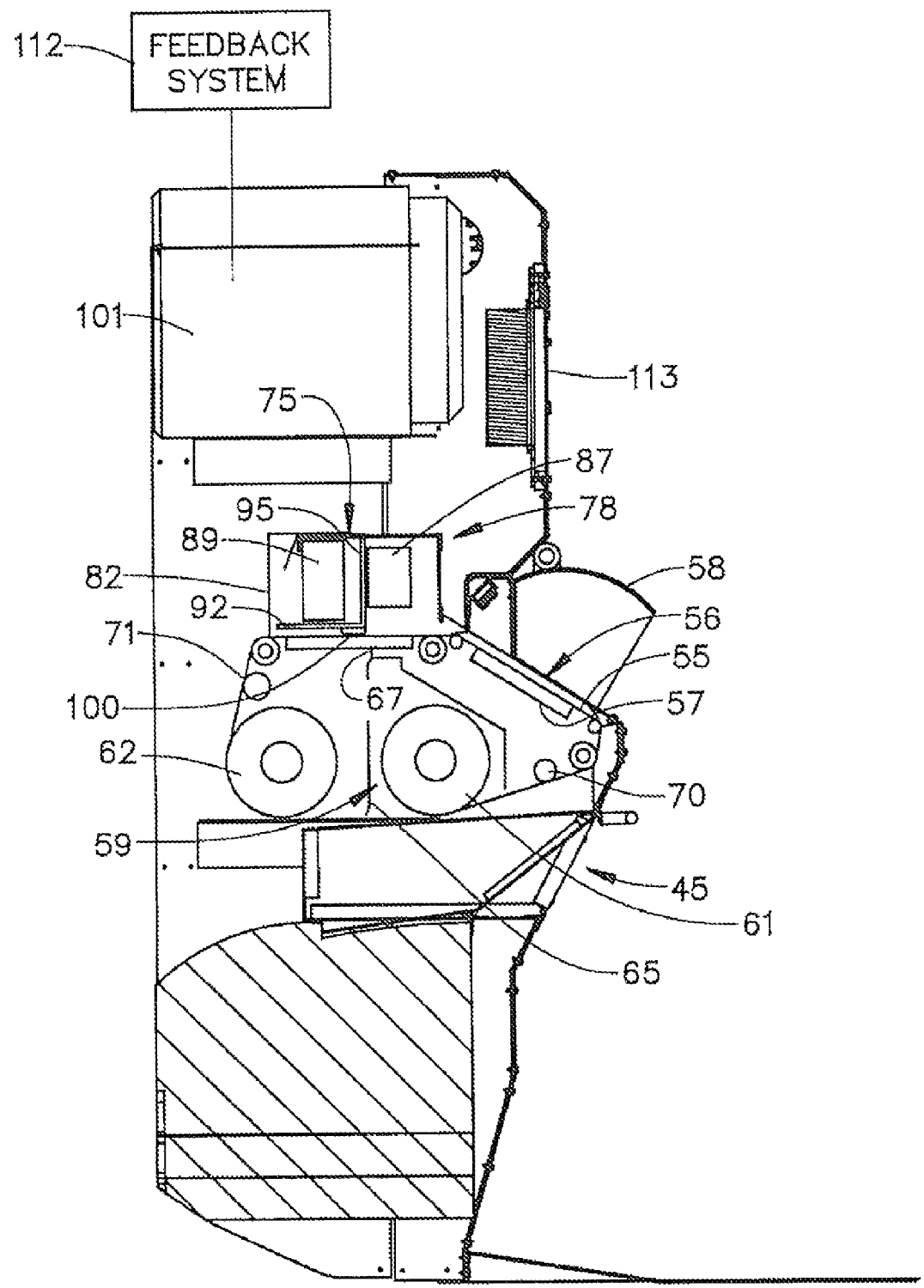
FIG. 2 is a cross-sectional side view of the screening center of FIG. 1.

As will become more fully evident below, the present invention can take various forms in connection with scanning for various potential threats. However, initial reference is made to FIGS. 1 and 2 in describing a security screening center or kiosk 2 constructed in accordance with a preferred embodiment of the present invention. Screening center 2 includes a main housing 4 provided with a front wall 6, a rear wall 7, a top wall 8, a bottom wall or base 9 and opposing side walls 10 and 11. In addition, screening center 2 is provided with various accessories to enhance an overall aesthetic appearance of main housing 4 and help screening center 2 blend in or match a particular venue or location. For example, in the embodiment shown, screening center 2 is shown with a pair of columns 17 and 18, that, in connection with various colored plaques or murals (not shown) attached to either rear wall 7 or side walls 10 and 11, provide a readily adaptable enhanced aesthetic appearance to screening center 2 that matches or blends with the particular venue at which screening center 2 is deployed.

Screening center 2 includes a sample collecting portion 34 arranged within a housing 37 that retrieves trace residue samples and, in certain instances, demographic samples from a subject. As such, collecting portion 34 includes a residue sample collector 38, a demographic sample collector (not shown) and an output portion 45 which, as will be described more fully below, outputs or issues an article to the subject upon completion of a screening process.

In accordance with the invention, residue sample collector 38 includes a sample collecting sheet 55 positioned upon a palm pad 56. A pressure or pad sensor 57 is arranged below palm pad 56 and, as will be detailed more fully below, functions to provide feedback to the subject during a sample collection process. In order to protect sample collecting sheet 55 from various environmental factors, palm pad 56 is positioned below a cowl 58. To ensure proper sample screening, fresh sampling media is provided for each screening process. Towards that end, sample collecting sheet 55 is provided on a continuous roll 59 including a first spool or new media portion 61 and a second spool or used media portion 62 which are separated by a shield 65 and a seal 67. Tension is applied to collection sheet 55 by a pair of tensioning rollers 70 and 71, while guide rollers (not separately labeled) are provided to ensure proper positioning upon palm pad 56. Application details of the overall structure operation and application for security center 2 can be found in commonly assigned U.S. patent application Ser. No. 11/418,193 filed on May 5, 2006, now U.S. Pat. No. 7,545,280, incorporated herein by reference.

In a manner that will be discussed more fully below, after obtaining a sample, sample collecting sheet 55 is moved to a sample processing system 75 including an analyzer portion 78. As shown, analyzer portion 78 includes a housing or light proof chamber 82 within which is positioned an applicator 87 and an image capturing unit or scanner 89. Arranged below image scanner 89 is a clear shield 92. Another shield 95 separates applicator 87 from image scanner 89. A heater 100 is mounted to an underside of clear shield 92. Heater 100 is activated when necessary to warm agents applied by applicator 87 or to warm the sample sheet to facilitate the screening process. In a manner that will be described more fully, below, during the screening process, analyzer portion 78 performs one of several pre-programmed scanning processes on the sample. The particular process employed depends upon various circumstances, such as desired accuracy, throughput or the presence of contaminants. In any case, following analysis of the sample, a controller portion 101 determines whether the sample contains a threat residue.

In order to ensure the collection of a proper sample, palm pad 56 includes pad sensor 57 having a pixel array 110 operatively coupled to controller 101. More specifically, upon approaching screening center 2, a test subject places his or her hand upon palm pad 56 and applies pressure to sample collection sheet 55. Preferably, sample collection sheet 55 is provided with an adhesive coating selected for moderate tackiness and skin contact compatibility and in order to minimize background fluorescence or luminescence. In addition, sample collection sheet 55 may have embedded therein various catalysts or precursors to support subsequent analysis or processing steps. For instance, zinc particulates or powder can be employed.

To ensure that sufficient pressure has been applied over a wide enough area for efficient sample recovery and to improve reproducibility of sample acquisition, screening center 2 includes a dynamic feedback system 112. If necessary, feedback system 112 provides visual and/or audible queues to the subject when additional pressure should be applied to palm pad 56. That is, the pressure applied to palm pad 56 must be of a sufficient force so as to obtain a suitable sample. Visual cues can be provided on a screen portion 113' provided in housing 4 or, as stated above, audible cues, such as "apply more pressure," can be signaled from screening center 2. In any event, once the subject has applied sufficient pressure, a proper sample 114 is obtained.

Figure 3:
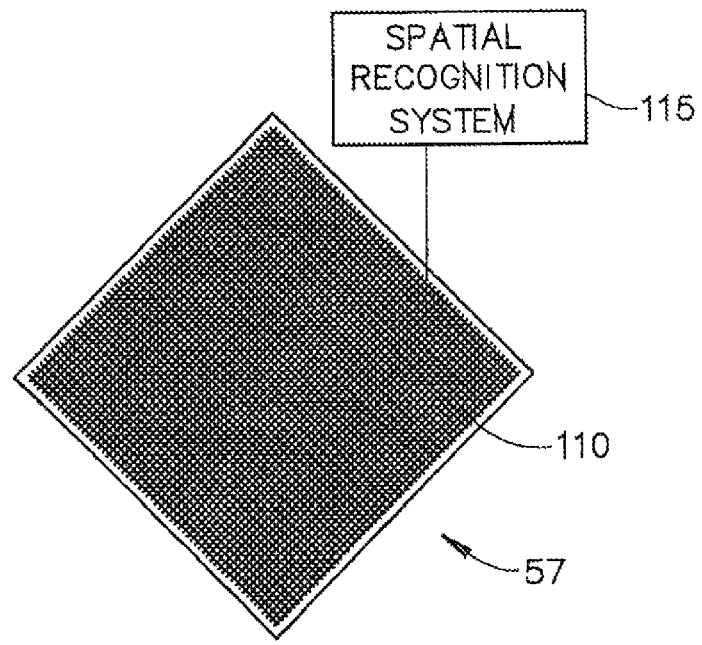
FIG. 3 is a detailed view of a palm sensor portion of the screening center.
Figure 4:
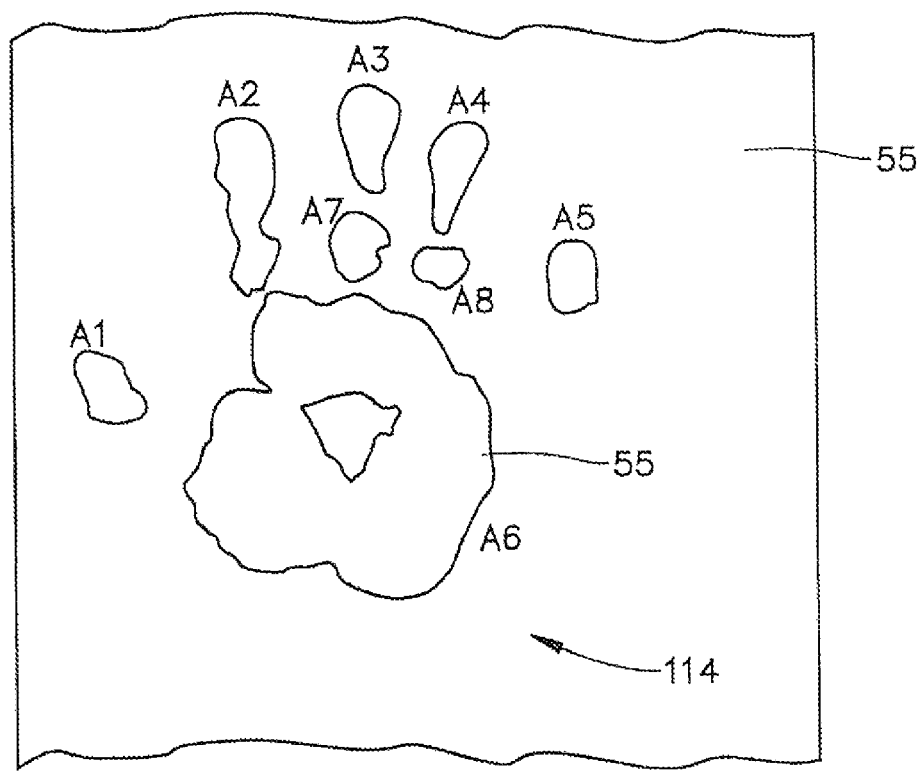
FIG. 4 is a representative view of a sample obtained during a screening process employing the screening center of FIG. 1.

In order to maximize sample analysis, screening center 2 also includes a spatial recognition system 115 (see FIG. 3) that performs a spatial analysis on sample 114. Spatial recognition system 115 utilizes pixel array 110 on pad sensor 57 to designate particular areas of interest on sample 114, such as A1-A8 (see FIG. 4). More specifically, studies have shown that particular portions of a hand are more likely to include trace residue than others. Thus, spatial recognition system 115 enables analyzer portion 78 to focus on particular points of interest A1-A8 of the obtained sample 114 in order to increase the reliability of the screening process. Once spatial analysis is complete, sample collection sheet 55 is shifted into analyzer portion 78 and the screening process continues.

Figure 5:
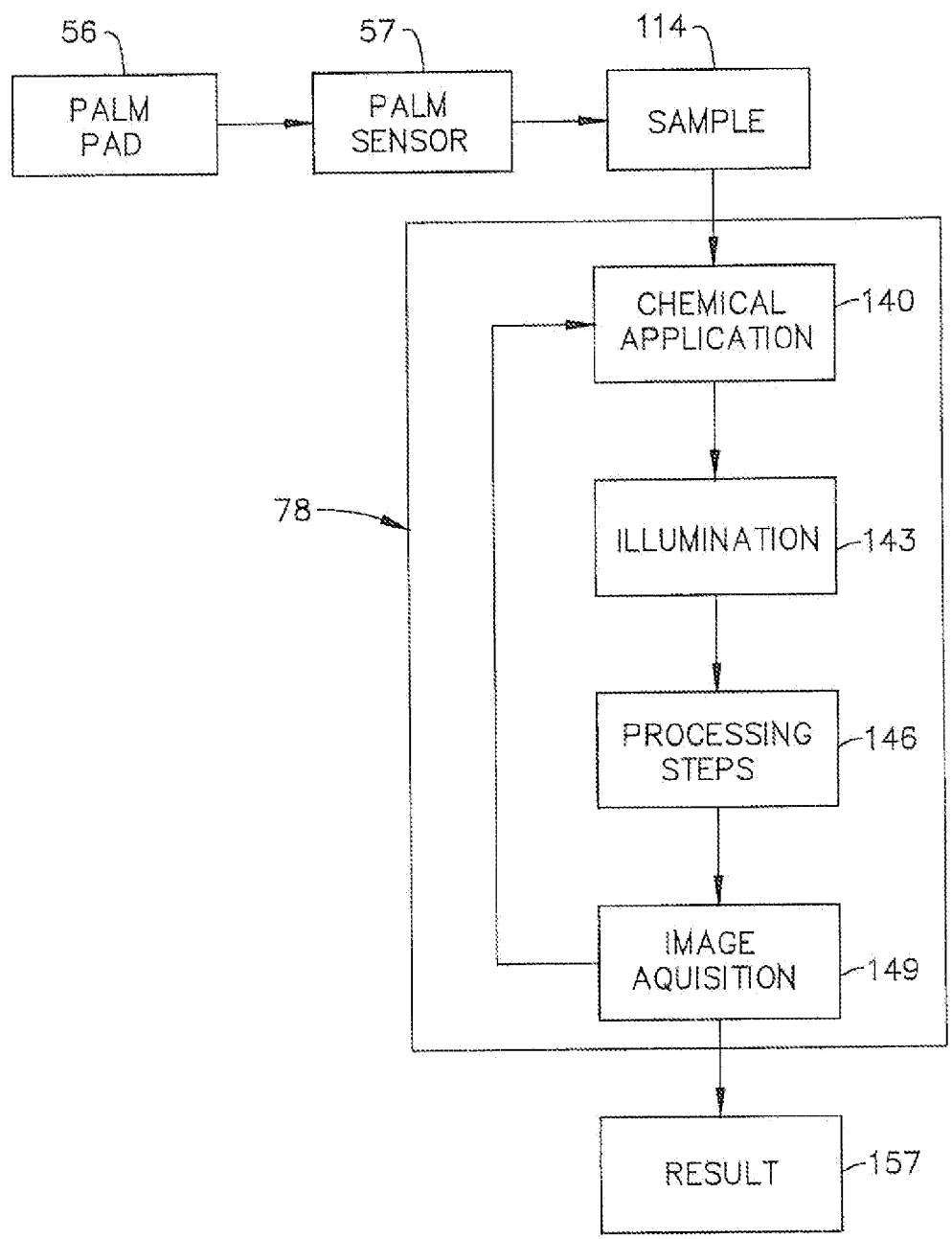
FIG. 5 is a block diagram outlining a screening process in accordance with one aspect of the present invention.

In accordance with the invention, analyzer portion 78 employs one or more processes when screening sample 114. The particular process employed depends upon a desired depth of analysis, a required level of throughput or other security demands. More specifically, if there is a need to maximize a probability detection, series processing, such as illustrated in FIG. 5, is preferably employed by analyzer portion 78. Alternatively, analyzer portion 78 can also be programmed to perform parallel processing (FIG. 6) when high throughput is desired. Finally, image processing, illustrated in FIG. 7, which digitally removes potentially interfering substances (or areas unlikely to contain the desired sample) from the detection process to compensate for process inconsistencies or background imperfections, can be employed, either alone or in combination with another analysis process. In general, image processing both increases detection accuracy and reduces false alarm rates.

As best shown in FIG. 5, serial processing involves sequentially passing sample 114 through a chemical application and illumination process. That is, after designating areas of interest A1-A8, sample collection sheet 55 is moved into analyzer portion 78 where a first chemical application process 140 is initiated. Following application of one or more chemical agents, sample collection sheet 55 is illuminated in step 143. Other processing steps, particularly the activation of heater 100 to activate a particular applied chemical agent or otherwise aid in analysis, are performed in step 146. After processing step 146 is complete, an image is acquired by image scanner 89 and analyzed for threat residue in step 149. This overall process can be repeated one or more times with different chemical applications, depending upon a desired level of accuracy and the particular trace residue of interest. Upon completion of series processing, analyzer portion 78 outputs a result 157 to controller 101. Result 157 can be presented to the test subject on a keepsake (not shown) that is issued through output portion 45 or, alternatively, passed to a central security station (not shown) for review and further analysis.

Figure 6:
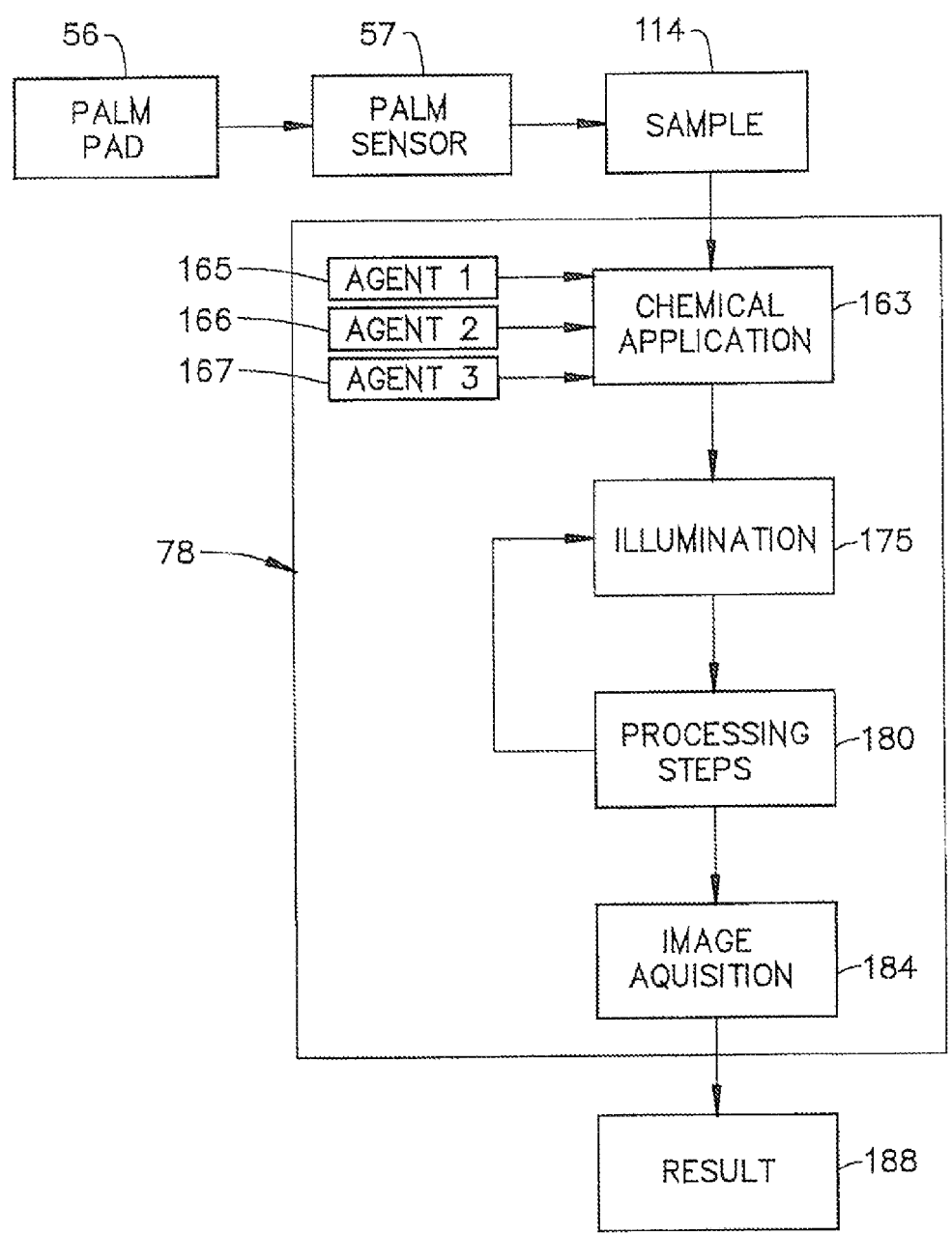
FIG. 6 is a block diagram outlining a screening process in accordance with another aspect of the present invention.

As stated above, if higher throughput is required, for example in order to expeditiously accommodate larger crowds, analyzer portion 78 can be programmed to perform parallel processing on sample 114. As best shown in FIG. 6, after designating areas of interest A1-A8, sample collection sheet 55 is passed to analyzer portion 78 for an initial chemical application process step 163. During chemical application process step 163, multiple chemical agents 165-167 are substantially simultaneously applied to sample collection sheet 55, even as it passes. Following chemical application process step 163, sample collection sheet 55 is illuminated in step 175 and subjected to various additional processing steps at 180, such as the activation of heater 100 to activate the chemical agents. Illumination step 175 and processing steps 180 can be repeated one or more times depending upon the chemicals employed and desired level of accuracy. After illumination and processing steps 175 and 180 are complete, an image is acquired during an image acquisition step 184. Once the image is obtained, analyzer portion 78 determines whether sample 114 contains a threat residue in step 188. The result is passed to controller 101 and, in a manner similar to that described above, either imprinted upon a keepsake which is issued to the tested subject or passed to a central control center.

Figure 7:
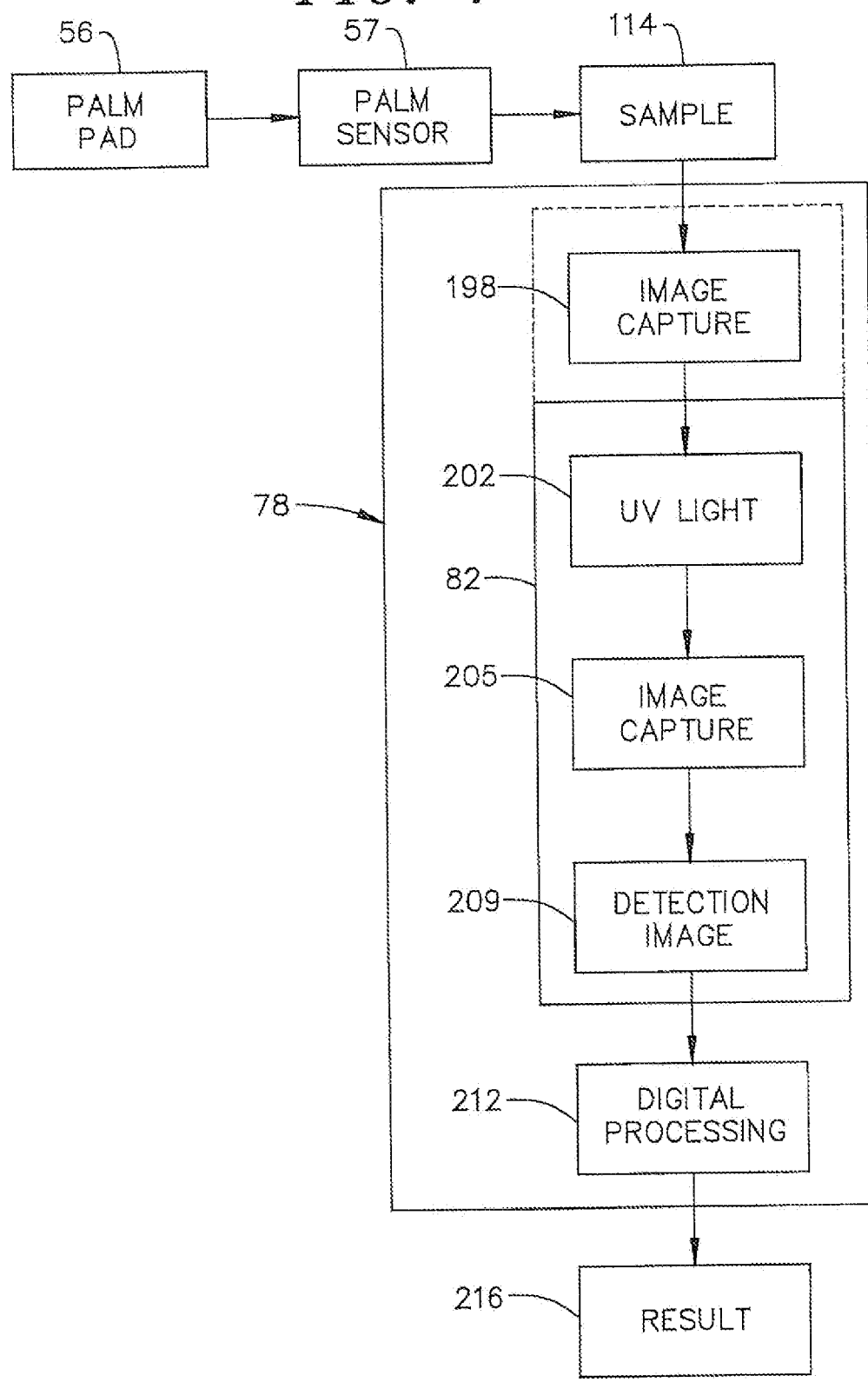
FIG. 7 is a block diagram outlining a screening process in accordance with yet another aspect of the present invention.

Reference will now be made to FIG. 7 in describing an image processing detection method employed by analyzer portion 78. In a manner similar to that described above, after designating areas of interest A1-A8, sample collection sheet 55 is passed to analyzer portion 78. At this point, a first image capture of sample 114 is performed in step 198. First image capture 198 is conducted employing white light. Preferably, image scanner 89 is configured to utilize a visible wavelength. The image obtained in step 198 is used to identify any physical contaminants that may be present on sample sheet 55 which might result in false alarms in the final result. Sample collection sheet 55 is then exposed to ultraviolet (UV) light in light proof chamber 82 in step 202. At this point, it should be noted that all image capture steps could be performed in light proof chamber 82, with only the particular type of illumination, i.e., white light, UV light, changing as necessary. In any case, while sample collection sheet is exposed to UV light, a second image is captured in step 205. Preferably, image scanner 89 is sensitive in a wavelength range that is specific for potential interference, such as white light contaminants that may fluoresce when subjected to UV light and contaminates that may absorb UV light. These potential interferences are image captured prior to step 209.

In step 209, a detection image is captured under the UV light using image scanner 89 which is preferably set to the same wavelength employed when capturing image 205. However, various other wavelengths can be chosen in order to optimize detecting optical changes consistent with trace explosive residues. In any event, once obtained, the three images are digitally analyzed in digital processing portion 212 for evidence of trace explosives. The images are correlated using one or more common reference points on all images. Preferably, the common reference points are registered in a calibration portion of internal hardware and software, but may also be registered using one or more of designated areas A1-A8 or pre-made marks on sample collection sheet 55.

The first images obtained in steps 198 and 205 are used to identify and remove any visible contaminants from the final image obtained in step 209. More specifically, the image obtained in step 209 is used to identify and remove any fluorescent and/or UV absorbing contaminants from the final image such that the known and identified contaminants are digitally removed from the detection image. The resulting image is then analyzed for evidence of trace explosive content. Once complete, the result is passed to controller 101 and, in a manner similar to that described above, either signified on a keepsake or passed to a central processing portion.

It should be recognized that the security screening center constructed in accordance with the present invention is readily adaptable to various venues and/or security levels employing one or more processing steps in order to ensure a high level of reliability while, simultaneously, increasing throughput through screening center 2. In addition, by providing feedback to test subjects to ensure proper sample recovery and employing a system that focuses on particular areas of a sample that are most likely to contain threat residue, the security system increases the likelihood of identifying potential threats. Furthermore, it should be realized that sample processing in accordance with the invention can be done on individual samples, such as with the various process steps described above being performed on a moving sample or in sample batches with multiple samples being concurrently processed.

Although described with reference to preferred embodiments of the invention, it should be readily understood that various changes and/or modifications can be made to the invention without departing from the spirit thereof. In general, the invention is only intended to be limited by the scope of the following claims.

We claim:

1. A method of obtaining and analyzing a sample from a subject through interaction with an interactive security screening system comprising:
    pressing an object associated with the subject upon a sample collection sheet positioned over a contact pad, said object exerting an amount of pressure upon the contact pad;
    sensing the amount of pressure applied to the contact pad through portions of the sample collection sheet;
    analyzing whether the amount of pressure sensed is sufficient to indicate that a proper sample has been obtained on the portions of the sample collection sheet; and
    analyzing the portions of the sample collection sheet with a sample processing system that scans the proper sample for threat residue.

2. The method of claim 1, further comprising: performing at least two cycles of chemical application followed by illumination in determining whether the sample collection sheet includes a threat residue.

3. The method of claim 1, further comprising:
    substantially simultaneously applying multiple chemical agents to the sample collections sheet;
    illuminating the sample collection sheet; and
    acquiring an image in determine whether the sample collection sheet includes a threat residue.

4. The method of claim 1, further comprising: capturing at least two images of the sample collection sheet.

5. The method of claim 4, further comprising: capturing each of the at least two images employing different wavelengths of light.

6. The method of claim 1, further comprising: selectively configuring the sample processing system to employ one of series processing, parallel processing and image processing.

7. The method of claim 1, further comprising: selectively re-configuring the sample processing system from employing one of series processing, parallel processing and image processing to another of series processing, parallel processing and image processing.

8. The method of claim 1, further comprising: providing a signal to the subject if a requisite amount of pressure is not applied to the sample collection sheet.

9. The method of claim 8, further comprising: providing one of an audio signal and a visual signal when the subject does not apply the requisite amount of pressure to the sample collection sheet.

10. The method of claim 1, wherein the sample collection sheet is taken from a roll of disposable sample collection sheets.

11. A method of obtaining and analyzing a sample from a subject through interaction with an interactive security screening system including a main housing, a contact pad provided on the main housing, a sample collection sheet positioned upon the contact pad, a pressure sensor operatively linked to the contact pad, a sample processing system and a spatial recognition system operatively connected to the sample processing system, said method comprising:
    receiving a trace residue sample upon contact of the sample collection sheet with a subject;
    utilizing the pressure sensor to determine a pressure applied to the contact pad by the subject during a sample collection process;
    utilizing the spatial recognition system to focus the sample processing system on particular portions of the sample collection sheet including the trace residue sample; and
    analyzing only the particular portions of the sample collection sheet with the sample processing system to determine whether the trace residue sample contains a threat residue.

12. The method of claim 11, further comprising: providing at least one of a visual signal and an audio signal concerning a proper sample collection through a feedback system operatively connected to the sensor.

13. The method of claim 11, further comprising: serially processing the sample through at least two cycles of chemical application and illumination.

14. The method of claim 11, further comprising: parallel processing the sample through at least one step wherein multiple chemical agents are substantially simultaneously applied to the sample collection sheet.

15. The method of claim 11, further comprising: image processing the sample through at least two image capture steps.

16. The method of claim 15, further comprising: employing illumination at two separate wavelengths in the at least two image capture steps respectively.

17. The method of claim 11, further comprising: employing one of series processing, parallel processing and image processing with the sample processing system.

18. The method of claim 11, further comprising: selectively activating a heater of the sample processing system to facilitate threat residue detection.

19. The method of claim 11, wherein the sample collection sheet is taken from a roll of disposable sample collection sheets.

20. A method of obtaining and analyzing a sample from a subject through interaction with an interactive security screening system comprising:

pressing an object associated with the subject upon a sample collection sheet positioned over a contact pad, said object exerting an amount of pressure upon the contact pad;

sensing the amount of pressure applied to the contact pad to assure that a proper sample has been obtained;

analyzing the sample collection sheet with a sample processing system that scans the proper sample for threat residue, wherein the sample processing system is only directed to particular portions of the sample sheet for scanning; and performing at least two cycles of chemical application followed by illumination in determining whether the sample collection sheet includes a threat residue.

* * * * *